(12) United States Patent
Hao et al.

(10) Patent No.: US 11,734,599 B2
(45) Date of Patent: Aug. 22, 2023

(54) FLEXIBLE USE OF A CLINICAL DECISION SUPPORT SYSTEM

(71) Applicant: Siemens Healthcare GmbH, Erlangen (DE)

(72) Inventors: Peng Hao, Nuremberg (DE); Philipp Hoelzer, Bubenreuth (DE); Razvan Ionasec, Nuremberg (DE)

(73) Assignee: Siemens Healthcare GmbH, Erlangen (DE)

(*) Notice: Subject to any disclaimer, the term of this patent is extended or adjusted under 35 U.S.C. 154(b) by 185 days.

(21) Appl. No.: 15/937,985

(22) Filed: Mar. 28, 2018

(65) Prior Publication Data

US 2018/0286515 A1 Oct. 4, 2018

(30) Foreign Application Priority Data

Apr. 4, 2017 (EP) .................................... 17164760

(51) Int. Cl.
  *G16H 50/20* (2018.01)
  *G16H 50/70* (2018.01)
  (Continued)

(52) U.S. Cl.
  CPC ............. *G06N 20/00* (2019.01); *A61B 6/032* (2013.01); *A61B 6/5205* (2013.01);
  (Continued)

(58) Field of Classification Search
  CPC ........ G16H 50/20; G16H 30/20; G16H 50/70; A61B 6/5217; A61B 6/032; A61B 6/5205; G06V 10/751
  See application file for complete search history.

(56) References Cited

U.S. PATENT DOCUMENTS

| 10,201,321 B2 | 2/2019 | Molloi |
| 2005/0020903 A1 | 1/2005 | Krishnan et al. |

(Continued)

FOREIGN PATENT DOCUMENTS

| CN | 1914617 A | 2/2007 |
| CN | 102551756 A | 7/2012 |
| CN | 104025119 A | 9/2014 |

OTHER PUBLICATIONS

"Thoracic Imaging Procedures", Computed Tomographie for Technologists 2010, Chapter 20, A Comprehensive Text.
(Continued)

*Primary Examiner* — Sheetal R Paulson
(74) *Attorney, Agent, or Firm* — Harness, Dickey & Pierce, P.L.C.

(57) ABSTRACT

A method is for adapting method steps for finding a result in a CT-based decision support method to the evaluation of LDCT image datasets. In an embodiment of the method, a plurality of reference image datasets are acquired from a plurality of patients. A reference image dataset features at least one CT image dataset from one of the plurality of patients and an LDCT dataset from the patient. Furthermore, method steps for establishing result data are applied to the different image datasets of the reference image datasets. The result data is compared with one another and the method steps for establishing result data are adapted based upon a result of the comparison to the establishing of result data with reference to an LDCT image dataset. An LDCT-based decision support method is also described. Moreover an adaptation device is described. A system for LDCT-based decision support is further described.

16 Claims, 3 Drawing Sheets

(51) Int. Cl.

| | |
|---|---|
| *A61B 6/03* | (2006.01) |
| *G16H 30/20* | (2018.01) |
| *G06N 20/00* | (2019.01) |
| *A61B 6/00* | (2006.01) |
| *G06T 7/00* | (2017.01) |

(52) U.S. Cl.
CPC .......... *A61B 6/5217* (2013.01); *A61B 6/5235* (2013.01); *A61B 6/5258* (2013.01); *G06T 7/0014* (2013.01); *G16H 30/20* (2018.01); *G16H 50/20* (2018.01); *G16H 50/70* (2018.01); *A61B 6/503* (2013.01); *A61B 6/504* (2013.01); *A61B 6/505* (2013.01); *A61B 6/542* (2013.01); *G06T 2207/10081* (2013.01); *G06T 2207/30008* (2013.01); *G06T 2207/30048* (2013.01); *G06T 2207/30061* (2013.01); *G06T 2207/30096* (2013.01)

(56) References Cited

U.S. PATENT DOCUMENTS

| | | |
|---|---|---|
| 2014/0376701 A1 | 12/2014 | Kopperdahl et al. |
| 2015/0201895 A1 | 7/2015 | Suzuki |
| 2016/0292684 A1 | 10/2016 | Youn |
| 2016/0292864 A1* | 10/2016 | Dabbah ................ A61B 6/486 |
| 2018/0158215 A1* | 6/2018 | Pang ...................... G01T 7/005 |
| 2019/0328348 A1* | 10/2019 | De Man .................. G06N 3/08 |

OTHER PUBLICATIONS

Wernick M. N. et al.: „Machine Learning in Medical Imaging, IEEE signal processing magazine, Jul. 2010; 2010.

Nakazato R et al: "Coronary artery calcium scoring using a reduced tube ; voltage and radiation dose protocol with dual-source computed tomography", ; Journal of Cardiovascular Computed Tomography, Elsevier, Amsterdam, NL, Bd. 3, Nr. 6, pp. 394-400, XP026808420, ISSN: 1934-5925; 2009.

Suzuki Keji: "Pixel-Based Machine Learning in Medical Imaging", in: International Journal of Biomedical Imaging, vol. 2012, pp. 1-19; 2011.

Y. Lecun et al.: „Deep learning, nature review, doi: 10.1038/nature14539, 2015, vol. 521; 2015.

Willemink Martin J. et al: "Finding the optimal dose reduction and iterative ; reconstruction level for coronary calcium scoring"; Journal of Cardiovascular Computed Tomography, Elsevier, Amsterdam, NL, ; Bd. 10, Nr. 1, pp. 69-75, XP029388302, ISSN: 1934-5925, DOI:10.1016/J.JCCT.2015.08.004; 2015.

German Office Action for German Application No. 17164760.5 dated Nov. 22, 2017.

L. Qiu-sheng et al. 'Image reconstruction for CT based on compressed sensing and ART' *Optical Technique*, vol. 35, No. 3, 2009, pp. 422-425. (with English translation).

J. Chamberlin et al, 'Automated detection of lung nodules and coronary artery calcium using artificial intelligence on low-dose CT scans for lung cancer screening: accuracy and prognostic value' *BMC Medicine*, 19:55, 2021, pp. 1-14.

* cited by examiner

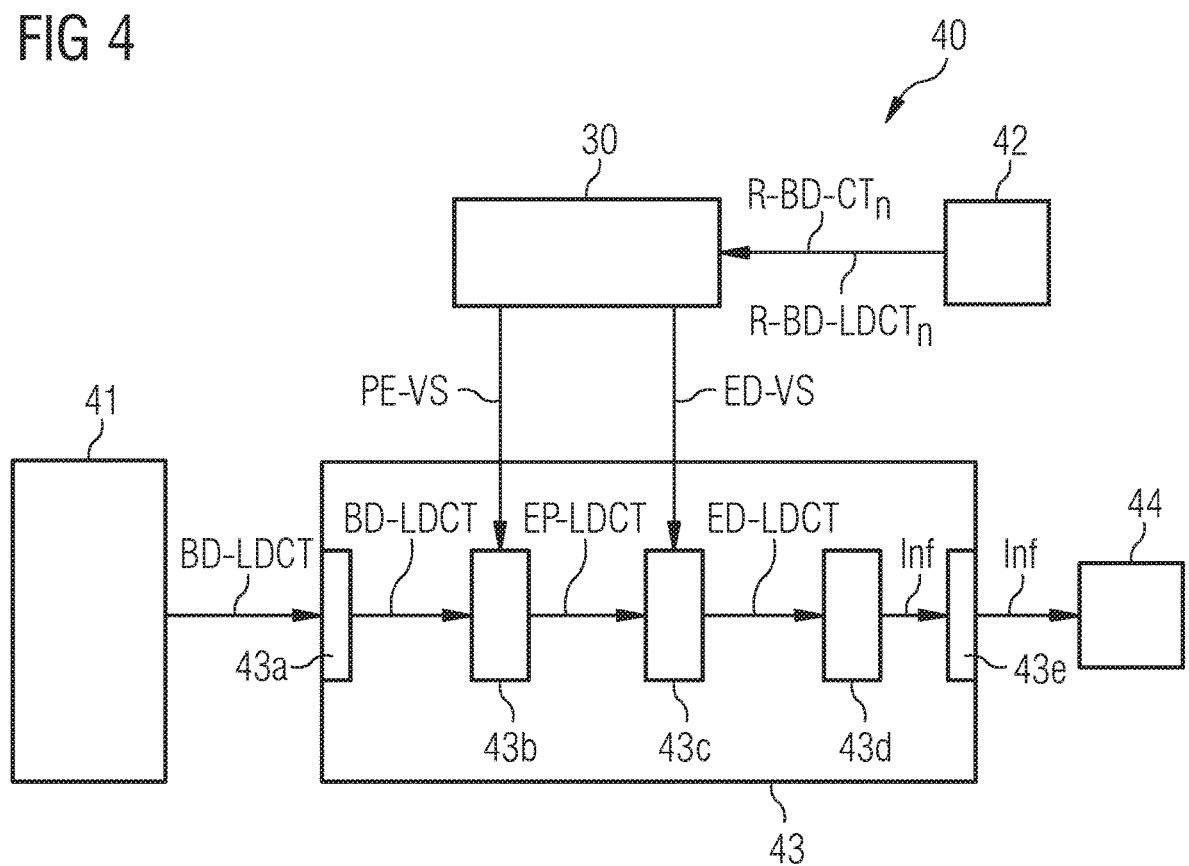

FLEXIBLE USE OF A CLINICAL DECISION SUPPORT SYSTEM

PRIORITY STATEMENT

The present application hereby claims priority under 35 U.S.C. § 119 to European patent application number EP 17164760.5 filed Apr. 4, 2017, the entire contents of which are hereby incorporated herein by reference.

FIELD

At least one embodiment of the invention generally relates to a method for adapting method steps for finding a result in a CT-based decision support method to the evaluation of LDCT image datasets. At least one embodiment of the invention further generally relates to an LDCT-based decision support method. Moreover at least one embodiment of the invention generally relates to an adaptation device. Finally, at least one embodiment of the invention further generally relates to a system for LDCT-based decision support.

BACKGROUND

Medical imaging methods are also used as part of early detection programs, in order to detect diseases before symptoms occur. The object of such examinations is to detect diseases in a state where they can be treated as well as possible at an earliest possible stage. Lung carcinomas are among the most difficult types of cancer to treat. It is therefore necessary to detect them as early as possible in such cases, in order to improve the result of the treatment.

An imaging method used in such cases is computed tomography (abbreviated to CT) of the chest region. Computed tomography is based on the acquisition of x-ray radiation, wherein so-called projection measurement data is created. In CT systems a combination of x-ray source and x-ray detector arranged opposite the source on a gantry normally circulates around a measurement space, in which the examination object (which will be referred to below, without any restriction on its general applicability, as the patient) is located. The center of rotation (also called the "isocenter") coincides in such cases with a so-called system axis z. During one or more orbits the patient is irradiated with x-ray radiation of the x-ray source, wherein, with the aid of the x-ray detector lying opposite thereto, projection measurement data or x-ray projection data is acquired. Image data, which is displayed to the user for appraisal, is then reconstructed on the basis of the projection measurement data.

In the use of computed tomography for detection of lung cancer a tumor can be detected at an earlier point in time than with conventional chest radiography. In the early detection of lung cancer persons having an increased risk of lung cancer, but not showing any symptoms of the disease, can be examined with the aid of a low-dose CT imaging method (abbreviated to LDCT method, LDCT=low dose CT), wherein images of the chest region will be recorded. In such an LDCT method images with sufficient quality are created to enable many diseases in the chest region to be detected, wherein a dose load of up to 90 percent lower is produced than with conventional CT chest imaging. Early detection programs for the detection of lung cancer are recommended in the USA for persons at risk. The risk for lung cancer depends in particular on the intensity of the smoking habits of a person, the dust load at their workplace and their age. Similar programs may well also be introduced in the future in Europe and Asia.

The LDCT thorax images that are created for the early detection of lung cancer also have valuable information relating to other diseases however. It would thus be desirable to use this information to detect other diseases of the thorax region of the patient and thus spare the patient additional CT examinations.

To date LDCT data has typically only been used for the early detection of lung cancer, wherein the process involves detecting lung nodes at an early stage. Other examinations relating to the thorax, such as for example tissue density measurements, lung volume calculations, measuring the volume of lung nodes, segmentation of the lungs, examination of the airways, measurement of the bone density of the spinal cord and other bones and calculations of the calcium score of the heart, cannot be applied directly to LDCT data, which has been created during imaging of the lungs for early detection of lung cancer. This LDCT data could however also be included in the diagnosis of other diseases, such as for example COPD, interstitial lung diseases, diseases of the coronary vessels and osteoporosis, or can even play a role in the planning of the therapy of the diseases.

SUMMARY

The inventors note that a few dedicated method steps are needed in particular during image data acquisition when establishing a calcium score and during measurements of the bone density, such as for example an acquisition of a bone phantom during bone density recording or the use of clocking of an image recording with an electrocardiogram during a measurement of a calcium score. Such dedicated method steps have previously prevented the re-use of LDCT data in these studies. Moreover the method steps used for evaluation with normal CT images cannot simply be transferred unmodified to LDCT images.

Thus, the inventors have discovered that a problem arises of designing an automated decision support, which can involve issues relating to a plurality of diseases in the thorax region, on the basis of image data, so that the examinations necessary therefor can be carried out while saving as much time as possible, in an effective manner and while protecting the patient and so that a sufficient quality of the decision-support data is still maintained.

Embodiments are directed to a method for adapting method steps for finding a result in a CT-based decision support method to the evaluation of LDCT image datasets; an LDCT-based decision support method; an adaptation device; and a system for LDCT-based decision support.

In at least one embodiment, a method is for adapting method steps for finding a result in a CT-based decision support method to the evaluation of LDCT image datasets. The method includes:

acquiring a plurality of reference image datasets from a plurality of patients, wherein a reference image dataset in each case at least has:
 a CT image dataset from one of the plurality of patients,
 an LDCT dataset from the patient;
applying method steps for establishing result data to the different image datasets of the reference image datasets;
comparing the result data with one another; and adapting the method steps for establishing result data to the establishing of result data with reference to an LDCT image dataset based upon a result of the comparison.

At least one embodiment of the inventive adaptation device has an input interface for acquiring a plurality of reference image datasets from a plurality of patients. A reference image dataset in each case comprises at least one CT image dataset from one of the plurality of patients and an LDCT dataset from the patient. Part of at least one embodiment of the inventive adaptation device is also a result data establishment unit for applying method steps for establishment of result data to the different image datasets of the reference image datasets. In addition at least one embodiment of the inventive adaptation device comprises a comparison unit for comparing the result data with one another. Moreover at least one embodiment of the inventive adaptation device has an adaptation unit for adapting the method steps for establishing result data to the establishment of result data with reference to an LDCT image dataset based upon a result of the comparison.

At least one embodiment of the inventive system for LDCT-based decision support has an LDCT imaging device. An LDCT imaging device is to be understood as a CT imaging device that is suitable for carrying out so-called LDCT imaging. The LDCT imaging device is configured for acquiring LDCT projection measurement data from a patient. The LDCT imaging device is further configured for reconstructing LDCT image data based upon the acquired LDCT projection measurement data. A decision support device is also part of at least one embodiment of the inventive system for LDCT-based decision support, which is configured to apply method steps for establishing result data, which have been adapted with the aid of a method of at least one embodiment, to the processing of LDCT image data, to the reconstructed LDCT image data. The inventive system for LDCT-based decision support also comprises an output unit for output of information for supporting a diagnosis decision. The information is based on the established result data and in the simplest case can comprise the result data for example.

A largely software-based realization has the advantage that computer systems already used previously for medical tasks can be upgraded in a simple manner by a software update in order to work in at least one embodiment of the inventive way as an adaptation device and/or decision support device. To this extent at least one embodiment is directed to a corresponding computer program product with a computer program, which is able to be loaded directly into a memory device of such a computer system, with program sections for carrying out all steps of at least one embodiment of the inventive method when the computer program is executed in the computer system.

Such a computer program product, as well as the computer program, can if necessary comprise additional elements, such as e.g. documentation and/or additional components, also hardware components, such as e.g. hardware keys (dongles etc.) for using the software.

For transport to the memory device of the computer system and/or for storage on the computer system a computer-readable medium, for example a memory stick, a hard disk or another transportable or permanently installed data medium can be used, on which the program sections of the computer program able to be read in and executed by a computer unit are stored. The computer unit can have one or more microprocessors or the like working together for this purpose for example.

BRIEF DESCRIPTION OF THE DRAWINGS

The invention will be explained once more in detail below with reference to the enclosed figures based upon example embodiments. In the figures:

FIG. 4 shows a block diagram, which comprises a device for LDCT-based decision support in accordance with an example embodiment of the invention.

DETAILED DESCRIPTION OF THE EXAMPLE EMBODIMENTS

Figure 1:
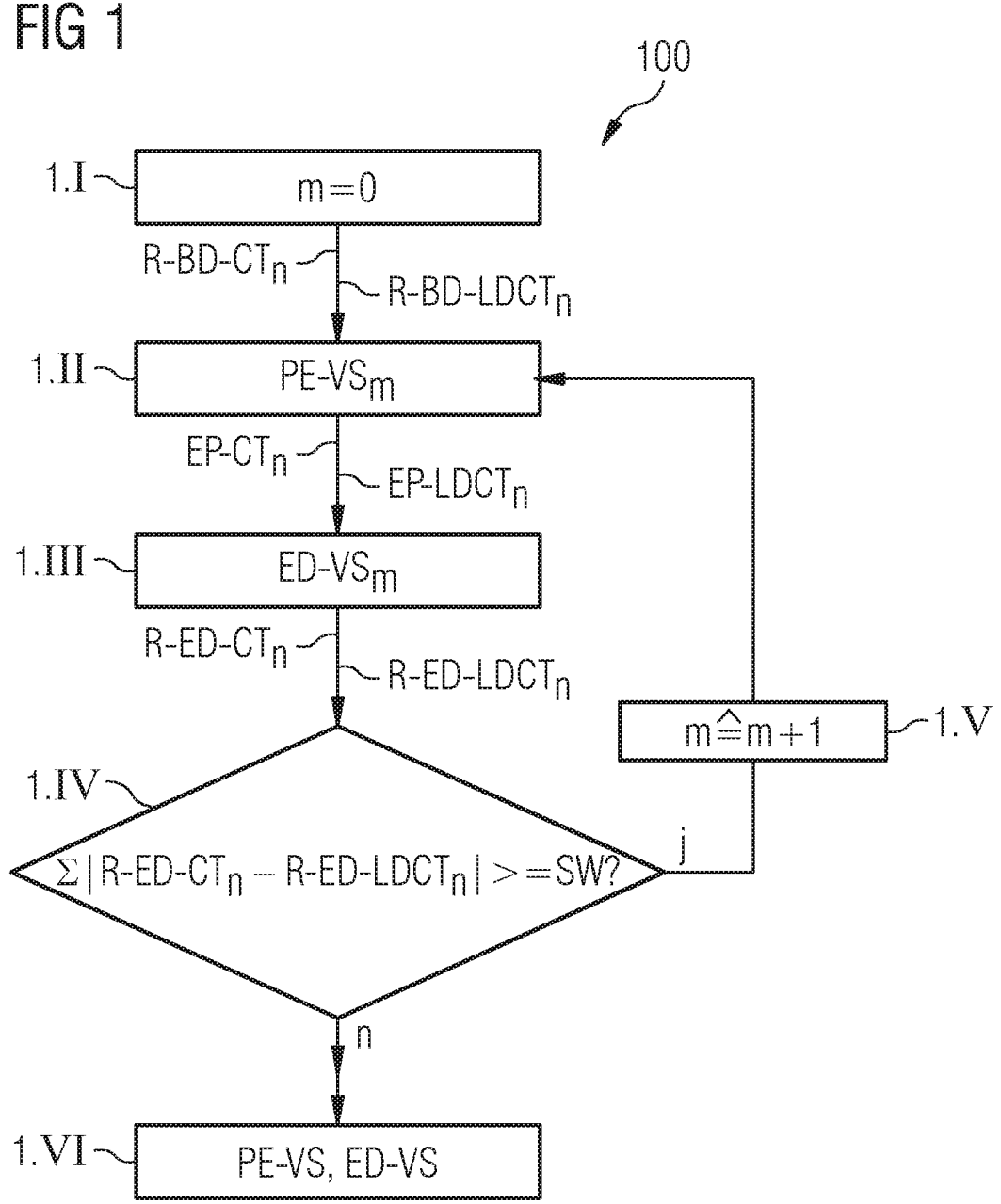
FIG. 1 shows a flow diagram, which illustrates a method for adapting a parameter extraction of a CT-based decision support method to the evaluation of LDCT image datasets in accordance with an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, in the inventive method for adapting method steps for finding a result in a CT-based decision support method to the evaluation of LDCT image datasets, a plurality of reference image datasets are acquired from a plurality of patients. In such cases a reference image dataset in each case has at least one CT image dataset from one of the plurality of patients and in addition an LDCT dataset from this patient. For example the two image datasets form a certain region of the body, preferably the same region of the body, of the respective patient. Especially preferably the respective imaged region of the body imaged comprises the thorax of the respective patient.

In each case the CT image dataset, which is used by default in a CT-based decision support method, offers a comparison option in the adaptation of method steps for finding a result to the evaluation of LDCT images. The reference image data forms a reference database, which is used for adapting the CT-based decision support method to the evaluation of LDCT image data. The inventive method is based on a decision support method being available for one or more medical issues, for example the diagnosis of diseases, on the basis of CT image data. These already known method steps are now to be adapted for the same issues to the processing of LDCT image data.

Furthermore method steps for establishing result data are then applied to the different image datasets of the reference image datasets. I.e. method steps of a previously-known CT-based decision support method are now applied both to the CT image data and also to the LDCT image data. Since the method steps function reliably for the CT image data, the result data obtained on the basis of the CT image data can subsequently be used for a comparison for checking the reliability of the method steps in the evaluation of LDCT image data. Result data is to be understood as data that is established in an automated manner within the framework of the decision support method for the aim of finding a result on the basis of evaluated image data. Result data can be assigned for example to specific pathologies to be detected, to which specific diseases are assigned.

As already mentioned, there is also a comparison of the result data, which was obtained on the basis of the CT image data and the result data, which was obtained on the basis of the LDCT image data. Advantageously deviations during the result finding on the basis of the LDCT image data can now be established. These deviations will be used during the further course of the method to adapt the method steps for establishing result data to the establishment of result data on the basis of an LDCT image dataset.

In this way an LDCT-based decision support method is created, which, depending on which types of result data are included in the comparison within the framework of the training or the adaptation, can be used for different medical issues.

Preferably, at least one embodiment of the inventive method is used to train the evaluation of LDCT image datasets in relation to result data, which can be used for decision support in a diagnosis of a disease other than lung cancer. As already explained, it has only previously been possible to use LDCT image data for detection of lung cancer. With at least one embodiment of the inventive method, it is now made possible also to evaluate this LDCT image data in an automated manner as a symptom of other diseases. In this way the effort of examining the patient is reduced.

Moreover, as a result of the use of LDCT image data instead of CT image data, the radiation dose for the patient can be reduced. A multiple use of the LDCT image data makes it possible for the first time routinely to undertake an early detection of a plurality of diseases in the thorax region in a short period of time, without endangering the patient unnecessarily by too great a radiation load. The described method steps are preferably carried out automatically, in order to make the adaptation independent of the capabilities and knowledge of a user and to enable the adaptation to be carried out with the aid of a larger database of reference data in a time-saving and efficient manner. The use of a larger database makes it possible to improve the adaptation of the decision support method to the evaluation of LDCT image data.

In at least one embodiment of the inventive, LDCT-based decision support method LDCT projection measurement data is acquired from a patient, preferably from the thorax of a patient. LDCT image data is reconstructed on the basis of the acquired LDCT projection measurement data. Furthermore, within the framework of at least one embodiment of the inventive LDCT-based decision support method, method steps for establishing result data, which have been adapted with the aid of the inventive method for adapting method steps for finding a result in a CT-based decision support method to the evaluation of LDCT image datasets to the processing of LDCT image data, are applied to the reconstructed LDCT image data.

After use of the decision support method result data is available, on the basis of which information for supporting a diagnosis decision is transferred to the user. Advantageously at least one embodiment of the inventive LDCT-based decision support method, like previously-known CT-based decision support methods, can be applied to different medical issues, in particular can be used in the search for different disease phenomena. In such cases the evaluation in respect of the different issues can be done on the basis of one and the same LDCT image dataset, whereby the examination effort is greatly reduced and the dose load is likewise greatly reduced because of the use of the low-dose imaging method.

At least one embodiment of the inventive method can bring great benefits in particular for persons with a plurality of disease risks, for example heavy smokers, since the different health risks can be clarified with a smaller number of imaging processes, preferably just with a single low-dose LDCT imaging process, which enables the dose load on the patient to be kept low. This improvement allows the use of a plurality of early detection measures to appear viable in health terms for the first time in most cases. Also the described method steps of the decision support method are preferably carried out in an automated manner, in order to make the decision basis created independent of the individual views, capabilities and knowledge of experts and to enable the evaluation of the LDCT image data to be carried out in a time-saving and efficient manner.

At least one embodiment of the inventive adaptation device has an input interface for acquiring a plurality of reference image datasets from a plurality of patients. A reference image dataset in each case comprises at least one CT image dataset from one of the plurality of patients and an LDCT dataset from the patient. Part of at least one embodiment of the inventive adaptation device is also a result data establishment unit for applying method steps for establishment of result data to the different image datasets of the reference image datasets. In addition at least one embodiment of the inventive adaptation device comprises a comparison unit for comparing the result data with one another. Moreover at least one embodiment of the inventive adaptation device has an adaptation unit for adapting the method steps for establishing result data to the establishment of result data with reference to an LDCT image dataset on the basis of a result of the comparison.

The result data establishment unit can comprise a parameter extraction unit for applying a method step for parameter extraction to the different image datasets of the reference image datasets for example. Parameter datasets are obtained in each case during the parameter extraction. A result data calculation unit, which is likewise part of the result data establishment unit, can then be employed for establishing result data on the basis of the extracted parameter datasets.

At least one embodiment of the inventive system for LDCT-based decision support has an LDCT imaging device. An LDCT imaging device is to be understood as a CT imaging device that is suitable for carrying out so-called LDCT imaging. The LDCT imaging device is configured for acquiring LDCT projection measurement data from a patient. The LDCT imaging device is further configured for reconstructing LDCT image data on the basis of the acquired LDCT projection measurement data. A decision support device is also part of at least one embodiment of the inventive system for LDCT-based decision support, which is configured to apply method steps for establishing result data, which have been adapted with the aid of a method of at least one embodiment, to the processing of LDCT image data, to the reconstructed LDCT image data. The inventive system for LDCT-based decision support also comprises an output unit for output of information for supporting a diagnosis decision. The information is based on the established result data and in the simplest case can comprise the result data for example.

The major components of at least one embodiment of the inventive adaptation device and parts of the system for LDCT-based decision support can be embodied for the most part in the form of software components. This relates in particular to parts of the result data establishment unit, the comparison unit and the adaptation unit of the adaptation device and parts of the decision support device. Basically however some of these components can also be realized, especially when particularly fast calculations are involved, in the form of software-supported hardware, for example FPGAs or the like. Likewise the interfaces needed, for example if only a transfer of data from other software components is involved, can be embodied as software interfaces. However they can also be embodied as interfaces constructed in hardware, which are controlled by suitable software.

A largely software-based realization has the advantage that computer systems already used previously for medical tasks can be upgraded in a simple manner by a software update in order to work in at least one embodiment of the inventive way as an adaptation device and/or decision support device. To this extent at least one embodiment is directed to a corresponding computer program product with a computer program, which is able to be loaded directly into a memory device of such a computer system, with program sections for carrying out all steps of at least one embodiment of the inventive method when the computer program is executed in the computer system.

Such a computer program product, as well as the computer program, can if necessary comprise additional elements, such as e.g. documentation and/or additional components, also hardware components, such as e.g. hardware keys (dongles etc.) for using the software.

For transport to the memory device of the computer system and/or for storage on the computer system a computer-readable medium, for example a memory stick, a hard disk or another transportable or permanently installed data medium can be used, on which the program sections of the computer program able to be read in and executed by a computer unit are stored. The computer unit can have one or more microprocessors or the like working together for this purpose for example.

The claims as well as the description given below each contain especially advantageous embodiments and developments of the invention. In this case the claims of one claim category can in particular also be developed in an analogous manner to the dependent claims of another claims category and their descriptive parts. In addition, within the framework of the invention, the various features of different example embodiments and claims can also be combined into new example embodiments.

In one embodiment of the inventive method for adapting method steps for finding a result in a CT-based decision support method to the evaluation of LDCT image datasets, the method steps for establishing result data are adapted such that the result data based thereon corresponds to the result data that has been established on the basis of the assigned CT image dataset. Thus, with the aid of the reference image data, a decision support method will be trained in the processing of LDCT image data until such time as the result data based on the LDCT image data no longer deviates by a predetermined degree from the result data that has been created on the basis of the corresponding CT image datasets. If the comparison is made with a sufficiently large database, it can be insured that the result data is correct in the evaluation of LDCT image data.

In one embodiment of the inventive method for adapting method steps for finding a result in a CT-based decision support method to the evaluation of LDCT image datasets, the method steps for establishing result data feature the following steps:

Application of a method step for parameter extraction to the different image datasets of the reference image datasets, wherein parameter datasets are obtained in each case, Application of a method step for establishing result data on the basis of the extracted parameter datasets.

Parameter extraction in this context is to be understood as establishing a parameter or parameter value based on an image dataset. Such a parameter can comprise a variable of a node, a surface or a volume and/or density of a calcification of vessel structures, contrast values, boundary lines or volume sizes established for a segmentation, for instance. Result data can then be established on the basis of these extracted parameters. Such result data comprises variables, which comprise information that can be used as a decision aid during the treatment of a medical issue. For example, on the basis of the established calcifications and their extent, a calcium score can be calculated as result data, which can then serve as a criterion for the risk of a heart attack. If lesions form the result data for example, then for example the threshold for the detection of a lesion can be changed. If for example in the evaluation of CT-based image data a completely closed outline, wherein the outline or its course forms the parameter to be extracted, were to be considered as necessary for the identification of a lesion, then during the evaluation of LDCT image data this criterion can be reduced to an only half closed outline. In this way the slightly lower image quality of the LDCT image data is compensated for.

In one embodiment of the inventive method for adapting method steps for finding a result in a CT-based decision support method to the evaluation of LDCT image datasets, the parameter extraction is preferably done such that the result data based thereon corresponds to the result data that has been established on the basis of the assigned CT image dataset. Expressed differently, in this variant embodiment, the evaluation of the LDCT image data is already adapted during the step of obtaining the parameters, on the basis of which the result data is then obtained.

In this variant embodiment, the process of parameter extraction is already adapted to the processing of LDCT image datasets and this is preferably done such that the parameters extracted on the basis of LDCT image datasets from one and the same patient correspond to the parameters that are established on the basis of CT image data from this patient.

Advantageously with this variant embodiment, in the evaluation step for creation of result data on the basis of the extracted parameters, there are fewer adaptation processes for adaptation to LDCT image data. For example such an adaptation can be undertaken to the extent that parameters or parameter values established on the basis of the LDCT image data are corrected such that they correspond to the parameters established on the basis of the CT image data as regards their value.

Expressed differently, the adaptation of the method step for parameter extraction is additionally based on a comparison of the extracted parameters, which have been obtained on the basis of the different image datasets. Examples for the adaptation of the parameter extraction can be the changing of the sensitivity during the segmentation of an object, for example a lesion. For example the necessary difference in contrast between lesion and surroundings can be reduced. Another type of adaptation relates to a correction of the established parameter values.

The adaptation of the method steps for establishing result data to the establishing of result data with reference to an LDCT image dataset can comprise both the adaptation of the method step for parameter extraction to the parameter extraction from an LDCT dataset and also the adaptation of the method step for establishing result data to the establishing of result data with reference to an LDCT image dataset. Thus both the step of parameter extraction and also the evaluation for creation of the result data can be adapted accordingly. This advantageously produces a number of adaptation options for adapting the evaluation of the LDCT image datasets accordingly.

In an example embodiment of the inventive method for adapting method steps for finding a result in a CT-based decision support method to the evaluation of LDCT image datasets the result data represents a decision aid in the diagnosis of at least one of the following diseases:
Pulmonary emphysema,
Respiratory diseases,
Interstitial lung diseases,
Cardiovascular disease,
Osteoporosis,
Cancers,
Bone damage.

Tin filters can be used in the acquisition of the LDCT projection measurement data for the LDCT image data for example, through which low-energy portions are preferably allowed to pass. With these tin filters an improved image quality and a lower dose load can be achieved.

In order to compensate for movement of the heart in the case of heart imaging, CT systems with reduced minimum achievable rotation time per recorded image or frame time can be used for example, whereby an improved resolution will be achieved.

The diseases relate in particular to the thorax region of a patient. If a lung cancer examination is now carried out on the basis of LDCT imaging, then information about other disease profiles of the thorax can be obtained at the same time. Persons at risk of lung cancer, for example smokers or persons who are working in very dusty workplaces, additionally also exhibit high risks of the other the diseases in the thorax region. With this variant embodiment the decision support method will be expanded to these additional disease profiles, so that the advantages of an early detection can also be used for these diseases, without having to carry out additional imaging and thus having to take account of the accompanying radiation loads.

In an especially preferred example embodiment of the inventive method for adapting method steps for finding a result in a CT-based decision support method to the evaluation of LDCT image datasets the result data comprises one of the following items of information:
The lung tissue density,
Bronchial wall analysis data,
Tissue patterns of the lungs to be recognized,
The calcium score,
The myocard fat,
The myocard size,
The bone density,
Texture features
Bone structure data.

Specific technical requirements have to be fulfilled during imaging in order to obtain specific result data. Such requirements are described for example in Chapter 20, "Thoracic Imaging Procedures", Computed Tomography for Technologists 2010, A Comprehensive Text, the entire contents of which are hereby incorporated herein by reference.

In the measurement of the bone density a calibration method with a calibration phantom or another type of reference measurement can be employed beforehand for example, in order to make deviation values independent of variations of the measurement conditions, such as for example properties of the scan units or of the patient geometry. Such a procedure is described for example in US 2014/0 376 701 A1, the entire contents of which are hereby incorporated herein by reference.

For the establishment of texture features detectors with an enhanced spatial resolution can be employed. For example photon-counting detectors are especially well suited to a higher resolution, since with these the resolution will not be reduced by so-called septa.

In order to make structures more easily visible, contrast media can also be administered before the recording of projection measurement data for creating the LDCT image datasets.

Advantageously, in the use of the additional measures when LDCT imaging is being carried out, information relating to a plurality of disease profiles in the thorax region can be obtained simultaneously with improved quality, without having to carry out additional imaging, in particular high-dose CT imaging.

In a variant embodiment of the inventive method for adapting method steps for finding a result in a CT-based decision support method to the evaluation of LDCT image datasets able to be applied in an especially meaningful way, the method steps for establishing result data are adapted to the establishing of result data with reference to an LDCT image dataset with the aid of an automatic learning method. Machine learning can be used to automate the adaptation process of the method steps for establishing result data to the evaluation of LDCT image data. The adaptation process to the processing of LDCT image datasets can be designed in such cases as a type of training method, in which there is a step-by-step approximation to a correct evaluation of LDCT image data on the basis of a training database. A particular type of machine learning is realized by so-called multilayer methods. Such methods are described for example in Y. LeCun et al "Deep learning", nature review, doi: 10.1038/nature14539 or in M. N. Wernick et al. "Machine Learning in Medical Imaging", IEEE signal processing magazine, July 2010, the entire contents of each of which are hereby incorporated herein by reference.

In an especially preferred example embodiment of the inventive method for adapting method steps for finding a result in a CT-based decision support method to the evaluation of LDCT image datasets, for the case in which after an adaptation of the method steps for establishing result data to the establishing of result data with reference to an LDCT image dataset on the basis of the CT image data and of the LDCT image data, partly different result data is created, a value for a probability for a correct establishment of result data is established on the basis of LDCT image data. I.e. the CT-based decision support method is not able to be adapted completely to the evaluation of LDCT image data, wherein even after the adaptation a degree of uncertainty remains during the creation of result data, the information about this uncertainty is also added to this result data, so that a user can decide for example whether to produce additional information, in particular additional image data, for example CT image data, in order to obtain a safe database for his diagnosis.

In a variant embodiment of the inventive LDCT-based decision support method, protocol parameters for the acquisition of LDCT projection measurement data are adapted to at least one disease to be diagnosed. In this context a protocol parameter is to be understood as a parameter of a measurement protocol, with which an imaging process can be adapted to individual requirements. For displaying specific examination regions for specific purposes for example, an especially strong contrast or an especially high temporal resolution can be selected, in order to fulfill information quality requirements.

During the imaging of the heart vessels, by shortening the frame time for example, the temporal resolution can be improved and the acquisition time can be shortened such that a kind of freezing of the heart movement is achieved. In this way heart imaging can be combined with an examination of another thorax region, for example the lungs. This enables an EKG-timed additional imaging of the heart to be dispensed with.

Illustrated in FIG. 1 is a method for adapting a CT-based decision support method to the evaluation of LDCT image datasets.

Initially, in step 1.I, a plurality of reference image datasets $R\text{-}BD_1, \ldots, R\text{-}BD_n, \ldots, R\text{-}BD_N$ from a plurality of patients $P_1, \ldots, P_n, \ldots, P_N$ is acquired from a database. Such a reference image dataset $R\text{-}BD_n$ comprises in each case both a CT image dataset $R\text{-}BD\text{-}CT_n$ and also a corresponding LDCT dataset $R\text{-}BD\text{-}LDCT_n$ of a patient $P_n$. The two reference sub-image datasets $R\text{-}BD\text{-}CT_n$, $R\text{-}BD\text{-}LDCT_n$ are recorded from the chest region of the patient $P_n$ in each case. For the reference image datasets $R\text{-}BD_n$ the parameter extraction method steps $PE\text{-}VS_0$ and the method steps $ED\text{-}VS_0$ used during the evaluation of the CT image datasets $R\text{-}BD\text{-}CT_n$ for result data formation are known. Furthermore the parameter data $EP\text{-}CT_n$ and result data $R\text{-}ED\text{-}CT_n$ established during a CT-based decision support method applied in each case to the CT image datasets $BD\text{-}CT_n$ are also known in each case. I.e., the method illustrated in FIG. 1 is based on a decision support method for one or more medical issues, for example the diagnosis of diseases, being available on the basis of CT image data.

Now, in step 1.II, with the aid of the parameter extraction method steps $PE\text{-}VS_0$ already known from application to the CT image datasets $R\text{-}BD\text{-}CT_n$, parameter data $EP\text{-}LDCT_n$ is extracted from the respective LDCT image datasets $R\text{-}BD\text{-}LDCT_n$. Such a parameter can involve regions in the imaging volume shaded by boundary lines or the like for example. Such a parameter can be very different, depending on the phenomena to be examined or the medical issue correlated therewith.

Subsequently, in step 1.III, result data $R\text{-}ED\text{-}LDCT_n$ is established on the basis of the extracted parameter data $EP\text{-}LDCT_n$. The result data $R\text{-}ED\text{-}LDCT_n$ can comprise an evaluation result of a decision-relevant variable for example. For example, on the basis of the shaded surfaces in the lung region established as evaluation result with the aid of the parameter extraction method step $PE\text{-}VS_0$, conclusions can be drawn about the size of lung nodes, on the basis of which a decision aid can be given for a diagnosis.

Advantageously the method concentrates in steps 1.II and 1.III on the extraction of parameter data or on the establishment of result data, which is relevant for one or more predetermined medical issues. This enables an LDCT image data-based decision support method possibly already suitable for a specific disease, for example lung cancer, to be adapted to the support of the diagnosis of other diseases that involve the thorax region.

The result data $R\text{-}ED\text{-}LDCT_n$ established on the basis of the LDCT image data $R\text{-}BD\text{-}LDCT_n$ is compared in step 1.IV with the previously known result data $R\text{-}ED\text{-}CT_n$ based on the corresponding CT image data $R\text{-}BD\text{-}CT_n$. For the case in which the totality of the established result data $R\text{-}ED\text{-}LDCT_n$ based on the LDCT image data $R\text{-}BD\text{-}LDCT_n$ deviates too greatly from the totality of the corresponding result data $R\text{-}ED\text{-}CT_n$, which was obtained on the basis of the CT image data $R\text{-}BD\text{-}CT_n$, which is indicated in FIG. 1 with "y", there is an adaptation in step 1.V of the parameter extraction method steps $PE\text{-}VS_0$ and of the steps $ED\text{-}VS_0$ for creation of result data, which have been applied to the LDCT image data $RE\text{-}LDCT_n$. The adaptation can be done for example within the framework of a machine learning method.

Then, with parameter extraction method steps $PE\text{-}VS_1$ adapted in this way, in step 1.II, parameter data $EP\text{-}LDCT_n$ can once again be extracted from the respective LDCT image datasets $R\text{-}BD\text{-}LDCT_n$ and in step 1.III result data RE-LDCT$_n$ is once again created on the basis of the extracted parameter data EP-LDCT$_n$. The method steps ED-VS$_1$ for result data formation necessary for this can likewise have been modified in step 1.V by adaptation. Subsequently, in step 1.IV, there is once again a comparison of the result data R-ED-LDCT$_n$ created on the basis of the LDCT image data R-BD-LDCT$_n$ with the corresponding result data R-ED-CT$_n$, which is known on the basis of the CT image datasets R-BD-CT$_n$.

If it is established in step 1.IV that the totality of the result data R-ED-LDCT$_n$ established on the basis of the LDCT image data R-BD-LDCT$_n$ no longer deviates by more than a certain degree SW from the totality of the result data R-ED-CT$_n$, which is assigned to the corresponding CT image data R-BD-CT$_n$, which is indicated in FIG. 1 with "n", then the method moves to step 1.VI, in which the last-used, adapted parameter extraction method steps PE-VS$_m$ and the last-used, adapted method steps ED-VS$_m$ for result data formation are defined as parameter extraction method steps PE-VS or method steps ED-VS suitable for an evaluation of LDCT image data. The method steps defined in this way can subsequently be employed in an LDCT-based decision support method. Depending on the type of the comparison material, i.e. in particular on the extracted parameters and result data of the CT image data, correspondingly adapted parameter extraction method steps PE-VS and method steps ED-VS$_m$ for establishing result data for the LDCT imaging can be created. This then enables the correspondingly adapted LDCT-based decision support method to be realized, with the aid of which, as well as lung cancer, other diseases involving the thorax can also be diagnosed.

Figure 2:
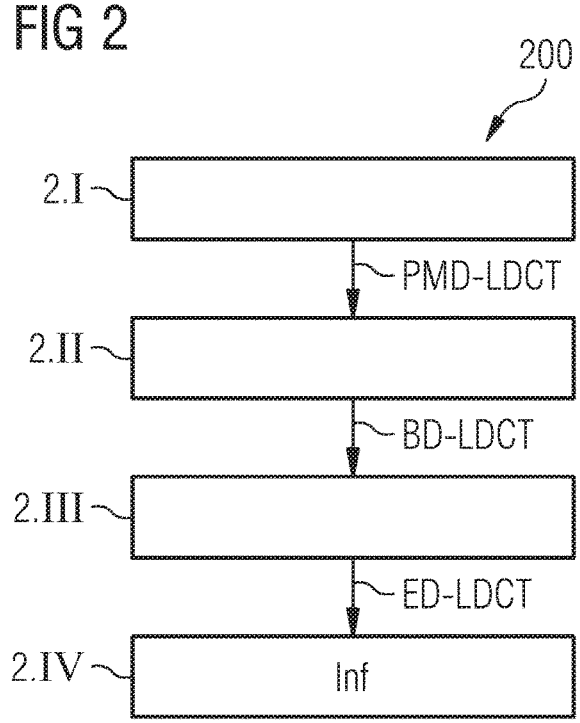
FIG. 2 shows a flow diagram, which illustrates an LDCT-based decision support method in accordance with an example embodiment of the invention.

FIG. 2 shows a flow diagram 200, which illustrates an LDCT-based decision support method in accordance with an example embodiment of the invention.

Initially, in step 2.I, projection measurement data PMD-LDCT is acquired from the thorax of a patient P with the aid of a computed tomography system LDCT. Subsequently, in step 2.II, LDCT image data BD-LDCT is reconstructed on the basis of the acquired LDCT projection measurement data PMD-LDCT. Then, in step 2.III, method steps PE-VS, ED-VS for establishing result data ED-LDCT are applied to the reconstructed image data BD-LDCT. The method steps PE-VS, ED-VS have been adapted with the method illustrated in FIG. 1 to the processing of LDCT image data BD-LDCT. Finally, in step 2.IV, information Inf for support of a diagnosis decision on the basis of the established result data ED-LDCT is output to a user.

Figure 3:
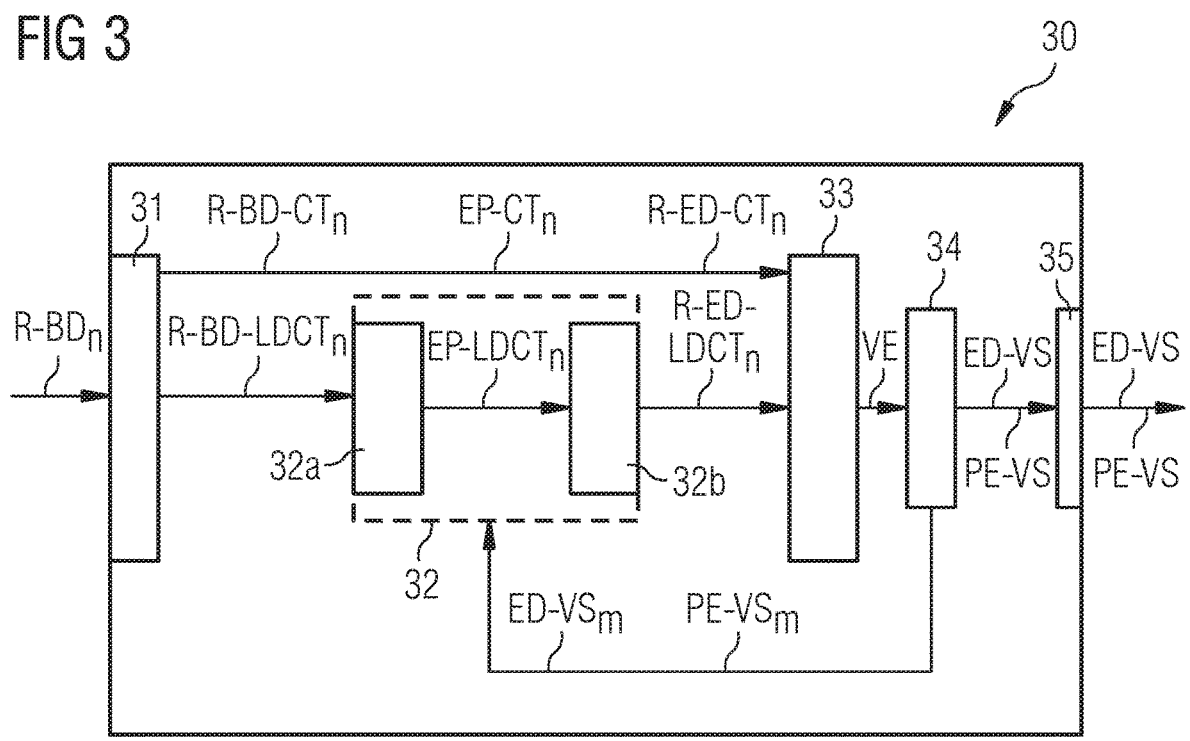
FIG. 3 shows a block diagram, with which an adaptation device is shown in accordance with an example embodiment of the invention.

Illustrated in FIG. 3 is an adaptation device 30 in accordance with an example embodiment of the invention. Such an adaptation device 30 comprises an input interface 31. The input interface 31 is configured to receive a plurality of reference image datasets R-BD$_n$ from a plurality of patients P$_n$. The reference image datasets R-BD$_n$ each comprise a CT image dataset R-BD-CT$_n$ from one of the plurality of patients and an LDCT dataset R-BD-LDCT$_n$ from the patient P$_n$. A result data establishment unit 32 is also part of the adaptation device 30. The result data establishment unit 32 is configured to create result data R-ED-LDCT$_n$ on the basis of the LDCT image datasets R-BD-LDCT$_n$. The reference image datasets R-BD$_n$, in addition to the CT image dataset R-BD-CT$_n$, also comprise corresponding result data R-ED-CT$_n$ and parameter datasets EP-CT$_n$, which have been obtained beforehand from the CT image datasets R-BD-CT$_n$.

The result data establishment unit 32 comprises a parameter extraction unit 32a for applying a method step for parameter extraction to the LDCT image datasets R-BD-LDCT$_n$ of the reference image datasets R-BD$_n$, wherein parameter datasets EP-LDCT$_n$ are obtained in each case. Then, on the basis of the parameter datasets EP-LDCT$_n$, result data R-ED-LDCT$_n$ is established through calculation by a result data calculation unit 32b.

The established result data R-ED-LDCT$_n$, which is based on the LDCT image data R-BD-LDCT$_n$, just like the previously-known result data R-ED-CT$_n$, which is based on the CT image data R-BD-CT$_n$, is transferred to a comparison unit 33, which is configured to compare result data R-ED-CT$_n$, R-ED-LDCT$_n$ with one another.

A comparison result VE is then transferred by the comparison unit 33 to an adaptation unit 34, which is configured for adapting method steps PE-VS$_0$, ED-VS$_0$ for establishing result data to the establishing of result data ED-LDCT$_n$ with reference to an LDCT image dataset BD-LDCT$_n$, R-BD-LDCT$_n$ on the basis of the comparison result VE. The adapted method steps PE-VS$_m$, ED-VS$_m$ can subsequently be tested with the aid of the result data establishment unit 32 and the comparison unit 33. If the comparison result established by the comparison unit 33 fulfills predefined quality criteria, i.e., if the result data ED-CT$_n$, ED-LDCT$_n$ still only deviates from one another by a maximum predetermined threshold value, then the adapted method steps PE-VS, ED-VS last established are output by the adaptation unit 34 via an output interface 35.

Shown schematically in FIG. 4 is a system 40 for LDCT-based decision support in accordance with an example embodiment of the invention. The system 40 comprises an LDCT imaging device 41, a database 42, a decision support device 43, a display unit 44 and an adaptation device 30 corresponding to the arrangement illustrated in FIG. 3. Initially, with the aid of the LDCT imaging device 41, projection measurement data PMD-LDCT is acquired from a patient. On the basis of the projection measurement data, LDCT image data BD-LDCT is reconstructed and transferred to the decision support device 43. There the LDCT image data BD-LDCT is received by an input interface 43a and passed on to a parameter extraction unit 43b, which is configured to apply method steps EP-VS for parameter extraction to the LDCT image datasets BD-LDCT$_n$, wherein parameter datasets EP-LDCT are obtained. Then, on the basis of the parameter datasets EP-LDCT, result data ED-LDCT is established through calculation by a result data calculation unit 43c and transferred to a unit 43d for creating information data. The parameter extraction unit 43b and the result data calculation unit 43c each obtain from the adaptation device 30 method step procedures PE-VS, ED-VS, specifically adapted to the processing of LD-CT image data, with which the parameter datasets EP-LDCT and result data ED-LDCT are established.

The information Inf created by the unit 43d for creation of information data Inf is subsequently output via an output interface 43e to the display unit 44 serving as an output unit. A user can then view the information displayed there as a decision aid for a diagnosis or a further treatment of a patient. The adaptation device 30 is connected to the database 42, which has stored reference image data R-BD$_n$, which features corresponding reference CT image datasets R-BD-CT$_n$ and reference LDCT image datasets R-BD-LDCT$_n$ in each case.

In conclusion, it is pointed out once again that the method and devices described above merely involve example embodiments of the invention and that the invention can be varied by the person skilled in the art without departing from the scope of the invention, provided the scope is predetermined by the claims. Thus the adaptation method has been described in the first instance in relation to an application in the region of the lungs. Embodiments of the invention are not restricted to the concrete application however, but can also basically be applied to a plurality of different medical issues involving the chest region. For the sake of completeness it is also pointed out that the use of the indefinite article "a" or "an" does not exclude the features involved also being present more than once. Likewise the term "unit" does not exclude the unit consisting of a number of components, which may if necessary also be physically distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for adapting a computerized tomography (CT) based decision support method for determining result data from a CT image dataset to a Low-Dose CT (LDCT) based decision support method for determining adapted result data from a LDCT image dataset the method comprising:
    acquiring a plurality of reference image datasets from a plurality of patients, each of the plurality of reference image datasets including at least:
        the CT image dataset from one of the plurality of patients, and
        the LDCT image dataset from the one of the plurality of patients;
    applying the CT-based decision support method to determine the result data of the CT image dataset and preliminary result data of the LDCT image dataset;
    comparing ones of the result data of the CT image dataset with ones of the preliminary result data of the LDCT image dataset; and
    adapting the CT-based decision support method to generate the LDCT-based decision support method in response to a result of the comparing indicating a difference between the result data of the CT image dataset and the preliminary result data of the LDCT image dataset is above a threshold.

2. The method of claim 1, wherein the applying the CT-based decision support method includes:
    extracting a parameter for each of CT image dataset and the LDCT image dataset, to respectively obtain parameter datasets; and
    establishing the result data for the CT image dataset and the preliminary result data for the LDCT image dataset based upon the respective extracted parameter datasets.

3. The method of claim 2, wherein the adapting the CT-based decision support method includes at least one of:
    adapting the extracting the parameter for the LDCT dataset; or
    adapting the establishing for reference to the LDCT image dataset.

4. The method of claim 3, wherein the result data and the adapted result data represents a decision aid in diagnosis of at least one of:
    pulmonary emphysema,
    respiratory diseases,
    interstitial lung diseases,
    cardiovascular disease,
    osteoporosis,
    cancers, and
    bone damage.

5. The method of claim 3, wherein the adapting the extracting the parameter is additionally based on a comparison of the extracted parameters.

6. The method of claim 3, wherein the parameter datasets extracted comprise one of:
    lung tissue density,
    bronchial wall analysis data,
    tissue patterns of the lungs to be recognized,
    calcium score,
    myocard fat,
    myocard size,
    bone density,
    texture features, and
    bone structure data.

7. The method of claim 2, wherein the adapting the extracting the parameter is additionally based on a comparison of the extracted parameters.

8. The method of claim 2, wherein the extracted parameter datasets comprise one of the following types of parameter:
    lung tissue density,
    bronchial wall analysis data,
    tissue patterns of lungs to be recognized,
    calcium score,
    myocard fat,
    myocard size,
    bone density,
    texture features, and
    bone structure data.

9. The method of claim 2, wherein the result data and the adapted result data represents a decision aid in diagnosis of at least one of:
    pulmonary emphysema,
    respiratory diseases,
    interstitial lung diseases,
    cardiovascular disease,
    osteoporosis,
    cancers, and
    bone damage.

10. The method of claim 2, wherein the adapting the CT-based decision support method is done with aid of a machine learning method.

11. The method of claim 2, further comprising:
determining a value for a probability of a correct determination of the preliminary result data in response to the preliminary result data being partly different from the result data.

12. The method of claim 1, wherein the result data and the adapted result data represents a decision aid in diagnosis of at least one of:
pulmonary emphysema,
respiratory diseases,
interstitial lung diseases,
cardiovascular disease,
osteoporosis,
cancers, and
bone damage.

13. The method of claim 1, wherein the adapting the CT-based decision support method is done with reference to the LDCT image dataset with the aid of a machine learning method.

14. The method of claim 1, further comprising:
determining a value for a probability of a correct determination of the preliminary result data in response to the preliminary result data being partly different from the result data.

15. An adaptation device, comprising:
an input interface configured to acquire a plurality of reference image datasets from a plurality of patients, each of the plurality of reference image datasets including at least:
a computerized tomography (CT) image dataset from one of the plurality of patients, and
a Low-Dose CT (LDCT) image dataset from a respective one of the plurality of patients;
a result data establishment unit configured to apply a CT-based decision support method for determining result data from a CT dataset to the CT image dataset and the LDCT image dataset;
a comparison unit to compare ones of the result data of the CT image dataset with ones of preliminary result data of the LDCT image dataset; and
an adaptation unit configured to adapt the CT-based decision support method to generate a LDCT-based decision support method for determining adapted result data from the LDCT image dataset, in response to a result of the comparison indicating a difference between the result data of the CT image dataset and the preliminary result data of the LDCT image dataset is above a threshold.

16. An adaptation device, comprising:
an input interface configured to acquire a plurality of reference image datasets from a plurality of patients, each of the plurality of reference image datasets including at least
a computerized tomography (CT) image dataset from one of the plurality of patients, and
a Low-Dose CT (LDCT) image dataset from a respective one of the plurality of patients;
a memory storing program computer-readable instructions; and
one or more processors configured to execute the computer-readable instructions such that the one or more processors are configured to
apply a CT-based decision support method for determining result data from CT image datasets to the CT image dataset to generate result data of the CT image dataset,
apply the CT-based decision support method to the LDCT image dataset to generate result data of the LDCT image dataset,
compare ones of the result data of the CT image dataset with ones of the result data of the LDCT image dataset, and
adapt the CT-based decision support method to generate a LDCT-based decision support method for determining adapted result data from the LDCT image dataset, in response to a result of the comparing indicating a difference between the result data of the CT image dataset and the preliminary result data of the LDCT image dataset is above a threshold.

* * * * *